United States Patent
Anciaux et al.

(10) Patent No.: US 6,849,772 B2
(45) Date of Patent: Feb. 1, 2005

(54) PROCESS FOR PRODUCING AND PURIFYING 1,1-DIFLUOROETHANE, AND PRODUCT THUS OBTAINED

(75) Inventors: Charles-Marie Anciaux, Tavaux (FR); Vincent Wilmet, Wavre (BE); Dominique Lecroc, Dole (FR)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 10/265,993

(22) Filed: Oct. 7, 2002

(65) Prior Publication Data

US 2003/0109759 A1 Jun. 12, 2003

Related U.S. Application Data

(62) Division of application No. 09/201,308, filed on Nov. 30, 1998, now abandoned.

(30) Foreign Application Priority Data

Dec. 1, 1997 (FR) ............................................. 97 15265

(51) Int. Cl.[7] ......................... C07C 17/00; C07C 17/08; C07C 19/08; C07C 17/38
(52) U.S. Cl. ...................... 570/164; 570/165; 570/166; 570/167; 570/168; 570/169; 570/177; 570/178; 203/80; 203/91
(58) Field of Search ............................... 570/164, 165, 570/166, 167, 168, 169, 177, 178; 203/80, 91

(56) References Cited

U.S. PATENT DOCUMENTS 2,452,975 A    11/1948   Whalley .................... 260/653
3,862,995 A    1/1975    Martens et al. ........... 200/653.6
5,396,001 A    3/1995    Pennetreau ................. 870/179
5,626,725 A  * 5/1997    Balthasart et al. ............ 203/91
5,714,652 A    2/1998    Grunchard et al. ......... 570/165
5,744,661 A    4/1998    Luly et al. ................. 570/177
5,874,657 A    2/1999    Miller et al. ............... 570/178

FOREIGN PATENT DOCUMENTS

| BE | 766395 | 10/1971 |
| CN | 1069019 | 2/1993 |
| CN | 1074434 | 7/1993 |
| EP | 0370688 | 5/1990 |
| EP | 0592711 | 4/1994 |
| EP | 0600536 | 6/1994 |
| EP | 0637579 | 2/1995 |
| EP | 0739875 | 10/1996 |
| RU | 2098399 | 12/1997 |
| SU | 341788 | 4/1997 |
| WO | 90/08750 | 8/1990 |
| WO | 96/40606 | 12/1996 |
| WO | 97/25300 | 7/1997 |

OTHER PUBLICATIONS 1,1–difluoroethane, *Dictionary of Chemical Engineering*, p. 17, 1992.

* cited by examiner

*Primary Examiner*—Elvis O. Price
(74) *Attorney, Agent, or Firm*—Connolly Bove Lodge & Hutz LLP

(57) ABSTRACT

1,1-Difluoroethane containing less than 10 mg/kg of vinyl chloride is obtained by treatment, with hydrogen fluoride, of a crude 1,1-difluoroethane containing less than 1 mol of hydrogen chloride per mole of 1,1-difluoroethane.

24 Claims, 2 Drawing Sheets

PROCESS FOR PRODUCING AND PURIFYING 1,1-DIFLUOROETHANE, AND PRODUCT THUS OBTAINED

This application is a divisional of U.S. application Ser. No. 09/201,308, filed Nov. 30, 1998, now abandoned.

The present invention relates to processes for producing and purifying 1,1-difluoroethane.

1,1-Difluoroethane (HFC-152a) is, for example, intended for use in swelling plastic foams (extrusion of polystyrene) or as a propellant in aerosols.

Processes for producing 1,1-difluoroethane by hydrofluorination of vinyl chloride (VC), 1-chloro-1-fluoroethane (HCFC-151a) or 1,1-dichloroethane (HCC-150a) have been known for a long time (see, for example, BE-A-766,395 and U.S. Pat. No. 2,452,975).

However, it has been observed that the known processes generally lead to a final product which is still contaminated to an unacceptable level with vinyl chloride.

It has consequently been attempted to overcome these drawbacks by subjecting the crude 1,1-difluoroethane obtained from the synthesis to a purification. Several techniques have been applied, among which mention may be made of hydrofluorination of the crude synthetic product.

Mention may be made in particular of a process for obtaining 1,1-difluoroethane by hydrofluorination of vinyl chloride in the presence of $SnCl_4$ with purification of the 1,1-difluoroethane obtained, by distillation in the presence of anhydrous hydrogen fluoride (inventor's certificate SU-341,788). However, more than 0.6% vinyl chloride remains in the HFC-152a thus obtained.

Mention may also be made of patent application WO-96/40606, in which the crude mixture obtained from the synthesis reactor is introduced directly into a step of reactive distillation in the presence of HF and optionally in the presence of a catalyst such as $SnCl_4$ or $BF_3$. The conditions in the distillation column are such that a mixture of purified HFC-152a and HCl are obtained at the top of the column and essentially HF, which is recycled into the reactor, is obtained at the bottom of the column.

It will readily be understood that, in this so-called "reactive distillation" column, one or more reactions therefore occur, simultaneously with the distillation, and that the behaviour of such a column for maintaining the optimum operating conditions will be complicated, especially in the presence of a catalyst.

Other techniques have also been proposed to purify 1,1-difluoroethane of any vinyl chloride. Mention may be made, inter alia, of the oxidation of vinyl chloride with various oxides (see EP-A-0,370,688), hydrogenation of vinyl chloride (see WO-90/08750), photochlorination of vinyl chloride (see abstract to CN-A-1,074,434 in Chemical Abstracts: 120: 269 634 k) and adsorption of vinyl chloride onto active charcoal (EP-A-0,600,536).

However, none of these processes makes it possible readily and continuously to obtain 1,1-difluoroethane permanently containing less than 10 mg of VC per kg of HFC-152a.

The aim of the present invention is to purify crude 1,1-difluoroethane such that it invariably has a very low content of vinyl chloride (preferably <10 mg/kg) and such that it is suitable for the applications for which this product is intended. Advantageously, this process will be simple and uncomplicated to carry out.

This problem is solved, according to the invention, by a process for purifying 1,1-difluoroethane of any vinyl chloride, comprising treatment of a crude 1,1-difluoroethane with hydrogen fluoride, which is characterized in that the crude 1,1-difluoroethane has, per mole of 1,1-difluoroethane, a hydrogen chloride (HCl) content of less than 1 mol, advantageously less than 0.5 mol, preferably less than 0.1 mol and even less than 0.03 mol. Usually, the vinyl chloride content in the 1,1-difluoroethane to be purified ranges between about 10 and about 20,000 mg/kg (ppm). However, the process according to the invention can also be used to purify 1,1-difluoroethane containing larger amounts of VC. Generally, it also has, per kg of 1,1-difluoroethane, a 1-chloro-1-fluoroethane content of less than 50 g, advantageously less than 10 g and preferably less than 5 g, and a 1,1-dichloroethane content of less than 20 g, advantageously less than 5 g and preferably less than 2 g. It generally contains, per kg of HFC-152a, from 2 to 500 g of HF, advantageously from 5 to 250 g, preferably from 10 to 200 g. Such a crude 1,1-difluoroethane is obtained, for example, by at least partially removing the hydrogen chloride contained in a crude reaction product resulting from the reaction between hydrogen fluoride and a chloro precursor of HFC-152a, such as vinyl chloride.

The present invention consequently also relates to a process for producing 1,1-difluoroethane, comprising a) a reaction between hydrogen fluoride and a chloro precursor of 1,1-difluoroethane, optionally in the presence of a hydrofluorination catalyst, this reaction giving rise to a crude reaction product, b) a separation of hydrogen chloride from the crude reaction product, and c) a further treatment of the crude reaction product, which is substantially depleted of HCl, with hydrogen fluoride, this further treatment giving rise to a formation of purified 1,1-difluoroethane.

The account hereinbelow focuses on this process for producing 1,1-difluoroethane from a chlorohydrocarbon. However, it is clear that all of the characteristics of the further treatment can also apply to the general process for purifying 1,1-difluoroethane mentioned above.

The solution proposed by the invention has the advantage of comprising, at the synthesis reactor outlet, a simple and common step of depletion of the hydrogen chloride content in the synthetic product obtained from the main reactor, and a further step in which the product obtained is subjected to a reaction similar to that which has taken place in the synthesis reactor, i.e. with hydrogen fluoride, so as to convert, entirely or almost entirely, the vinyl chloride still present in the reaction product.

The impossibility of achieving a vinyl chloride content of less than 10 mg/kg in 1,1-difluoroethane at the synthesis reactor outlet, even after a simple distillation of the HFC-152a produced, has been observed. The reason for this is that, in the latter case, an azeotrope forms between the vinyl chloride and the HFC-152a, these two compounds moreover having a very low relative volatility. A reactive distillation of the crude reaction product as obtained from the reactor, i.e. not depleted of HCl, does not increase the possibility of achieving very low vinyl chloride contents. The solution proposed according to the invention overcomes these drawbacks.

According to a preferred embodiment of the invention, the synthetic reaction takes place in the liquid phase in an organic solvent. In general, vinyl chloride is used as chloro precursor of 1,1-difluoroethane. Such a reaction has already been described in patent applications EP-A-0,637,579 and EP-A-0,739,875. It can also be envisaged to feed another chlorohydrocarbon into the synthesis reactor, in particular HCC-150a or HCFC-151a, in total or partial replacement for the vinyl chloride.

According to one embodiment of the invention, the HCl is separated from the crude reaction product obtained from the synthesis reactor by withdrawing the HCl from the top of a distillation column, from which the tail fraction is collected in order to subject it to the further treatment.

According to an improved embodiment of the invention, a product mainly containing 1,1-difluoroethane to be purified is extracted laterally from the said distillation column, while a product mainly containing products heavier than 1,1-difluoroethane, in particular HF and synthetic intermediates such as 1,1-chlorofluoroethane (HCFC-151a) and 1,1-dichloroethane (HCC-150a), are taken from the column tail fraction.

In this embodiment, the efficacy of the further treatment is improved appreciably by reducing the content of synthetic intermediates which are liable to reform vinyl chloride during the reaction. It can be envisaged to reduce this content of synthetic intermediates even further by inserting an additional distillation column between the HCl distillation and the further treatment and by conveying therein the reaction product which is substantially depleted of HCl. The insertion of a reflux column between the synthesis reactor and the HCl distillation column also improves this reduction into substances liable to reform vinyl chloride. In one variant, the HCl distillation column can consist merely of a head section, mounted on the hydrofluorination reactor which serves as a boiling vessel.

The further treatment can be carried out in the liquid phase or in the gas phase. Advantageously, it is carried out in the liquid phase, preferably in a reaction medium containing at least 200 g of HF per kg. In a particularly preferred manner, it is carried out in a liquid medium containing at least 500 g of HF per kg, or even at least 800 g per kg.

According to an advantageous embodiment of the invention, the further treatment takes place in the presence of a hydrofluorination catalyst, which is preferably the same as the one used in the synthetic reaction, if this reaction has used such a catalyst, or in any case a catalyst which can be used in the synthetic reaction.

As catalysts which can be used, mention may be made of derivatives of metals chosen from the metals from groups IIIa, IVa, IVb, Va, Vb and VIb of the Periodic Table of the Elements, and mixtures thereof. The tin, molybdenum, titanium, vanadium, antimony and tungsten derivatives are preferred. Tin derivatives are particularly suitable. Halides, such as chlorides, fluorides and chlorofluorides, as well as oxides and oxyhalides are preferably used as metal derivatives. $SnCl_4$ is most particularly preferred. In the liquid phase, the amount of catalyst to be provided, per liter of reaction medium, can be from about 0 to 1 mol, in particular from 0.1 to 200 mmol, advantageously from 0.2 to 100 mmol and preferably from 0.5 to 20 mmol.

When the further treatment is carried out in an organic solvent, this is preferably the same as the solvent for the synthetic reaction. As suitable organic solvent, mention may be made in particular of perchloroethylene or saturated halohydrocarbons, preferably chloro, fluoro or chlorofluorohydrocarbons containing from 1 to 8 carbon atoms, or mixtures thereof. Using the same catalyst, for example $SnCl_4$, in the synthetic reaction and the further treatment, the process is greatly simplified, and this is all the more the case since the further treatment can be carried out under similar conditions, in particular in a reactor in which the catalyst concentrations can be finely controlled, and the residence times required to obtain an optimum reaction can be determined precisely. Furthermore, since the further treatment does not use any chemical compound or reagent other than those already present in the synthetic reaction, it does not complicate the rest of the process for the purification of the purified 1,1-difluoroethane.

The crude reaction product, substantially depleted of HCl, which is used in the further treatment typically has a composition similar to that given above, for the crude 1,1-difluoroethane used in the general purification process. If necessary, HF can be added to the crude reaction product to be purified.

Advantageously, crude 1,1-difluoroethane is subjected to the further treatment continuously, at a flow rate typically of from 0.01 to 5 kg of crude 1,1-difluoroethane per hour and per liter of reaction medium, preferably from 0.05 to 2 kg.

Generally, the temperature at which the further treatment is carried out is at least 40° C. and does not exceed 130° C. Preferably, it is at least 50° C. and does not exceed 120° C. The pressure is chosen as a function of the temperature of the reaction mixture. It is generally at least equal to 2 bar. It usually does not exceed 50 bar.

The present invention also relates to 1,1-difluoroethane, obtained by hydrofluorination of a chlorohydrocarbon, which has a purity of greater than 99.8% by weight, preferably greater than 99.9% by weight, and a vinyl chloride content of less than 10 mg/kg, preferably less than 5 mg/kg, or even less than 2 mg/kg.

Other specific aims of the invention are indicated in the claims which follow.

Other details and particular features of the invention will also emerge from the description of a number of embodiments given below without any limitation and with reference to the attached drawings.

BRIEF DESCRIPTION OF THE DRAWINGS

EXAMPLE 1

Figure 1:
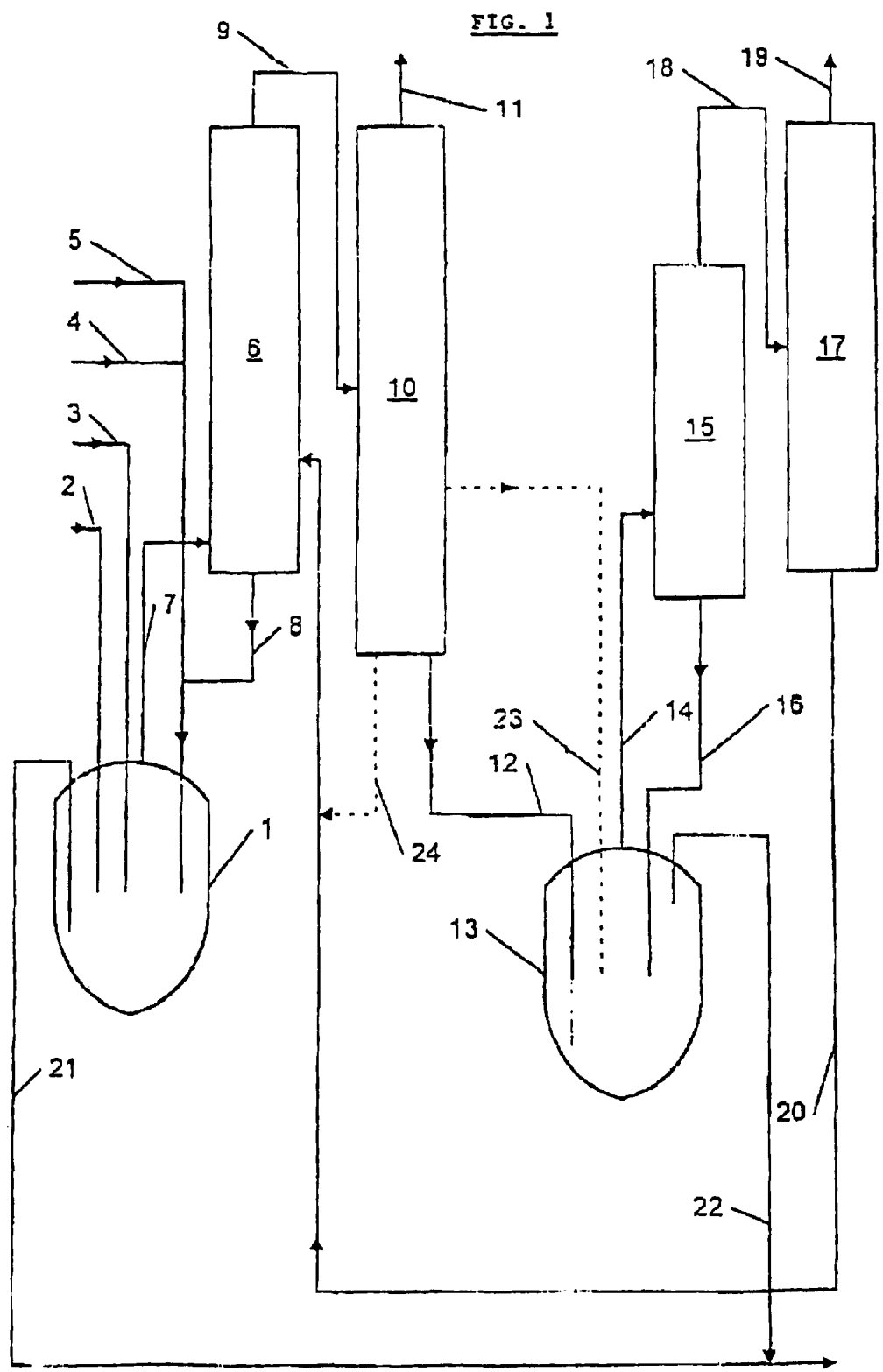

A plant for producing 1,1-difluoroethane according to the invention is illustrated diagrammatically in FIG. 1.

This figure shows a reactor 1 for the synthesis of 1,1-difluoroethane, fed with vinyl chloride via a feed pipe 2 and with hydrogen fluoride via another feed pipe 3. In the preferred embodiment illustrated, a catalyst is introduced into the reactor 1 via an inlet pipe 4 which opens into an organic solvent delivery pipe 5.

The synthetic reaction is carried out under known operating conditions. In this respect, reference may be made, for example, to patent applications EP-A-0,637,579 and EP-A-0,739,875.

Advantageously, a temperature and a pressure are established in the reactor such that the 1,1-difluoroethane formed leaves the liquid mixture in the reactor continuously, in the form of a gaseous, crude reaction product which is conveyed conventionally into a reflux column 6, via the pipe 7 provided at the top of reactor 1.

The synthesis reactor can be any known reactor which is capable of operating under the working conditions of the process. For example, a reactor heated by an oil bath—not represented—may be envisaged.

The reflux column 6 operates under conditions such that it allows recycling into the reactor, via the return pipe 8 which opens into the pipe 5, of most of the HCFC-151a and HCC-150a synthetic intermediates, as well as HF and any other components in the reaction medium, in particular organic solvent. The product in the head fraction of this reflux column 6 typically contains about 60% by weight of HFC-152a, about 30% by weight of HCl, about 10% by weight of HF, about 2 to 20 g/kg of HCFC-151a/HCC-150a and from a few tens (for example 20) to a few thousands of mg (for example 10,000) of vinyl chloride per kilo.

As may be observed, this head fraction leaving the reflux column via the pipe 9 is still highly contaminated with vinyl chloride and with synthetic intermediates.

The pipe 9 opens into an intermediate part of a distillation column 10 whose operating conditions are such that a separation of HCl in the gaseous state is obtained at the top of the column, this HCl being evacuated via the outlet pipe 11. A crude reaction product substantially depleted of HCl is withdrawn from the bottom of column 10 and is conveyed, via the pipe 12, to the post-reactor 13 in which the further treatment according to the invention is carried out.

The post-reactor 13 can be of the same type as the synthesis reactor 1. In the illustrated embodiment of the invention, the reaction medium therein is liquid and is composed essentially of hydrogen fluoride, optionally with an organic solvent in addition. Advantageously, a hydrofluorination catalyst is in the reaction medium of the post-reactor.

The vinyl chloride and the HCFC-151a and HCC-150a synthetic intermediates which are still contained in the tail fraction of the distillation column 10 are almost quantitatively converted into HFC-152a in the post-reactor 13. The vinyl chloride content relative to the HFC-152a leaving the post-reactor in gaseous form, via the pipe 14, is typically less than 1 mg/kg.

In the embodiment illustrated, it has been envisaged to pass the HFC-152a thus purified of VC into another reflux column 15, in which a fraction heavier than this substance is condensed and recycled into the post-reactor 13 via the return pipe 16.

The head fraction from the reflux column 15 can in addition be conveyed into an intermediate part of an additional distillation column 17 via a delivery pipe 18.

The purified HFC-152a escapes at the top of the distillation column 17 and is conveyed, via the outlet pipe 19, towards the optional additional treatments, which are known per se, of neutralization, drying and final distillation.

At the bottom of the column 17, a heavy fraction is collected in the pipe 20 and, in the example illustrated, is returned into the reflux column 6.

Heavy fractions are regularly purged from the two reactors 1 and 13 and are evacuated via the purge pipes 21 and 22.

EXAMPLE 2

In the plant represented in FIG. 1, an embodiment variant has been provided, which differs from the one described in Example 1 in that the pipe 12 is dispensed with.

In the plant according to the present example, a crude reaction product containing HFC-152a is extracted laterally from the distillation column 10, in the bottom of this column, and is conveyed into the post-reactor 13 via a pipe 23, represented by dotted lines. A pipe 24 fitted at the bottom of the column 10 and also represented by dotted lines allows a fraction heavier than HFC-152a, in particular synthetic intermediates of the latter, to be removed from the column and returned via the pipe 20 into the reflux column 6.

The reaction product introduced into the post-reactor 13 thus contains fewer synthetic intermediates capable of reforming vinyl chloride during reaction.

EXAMPLE 3

Figure 2:
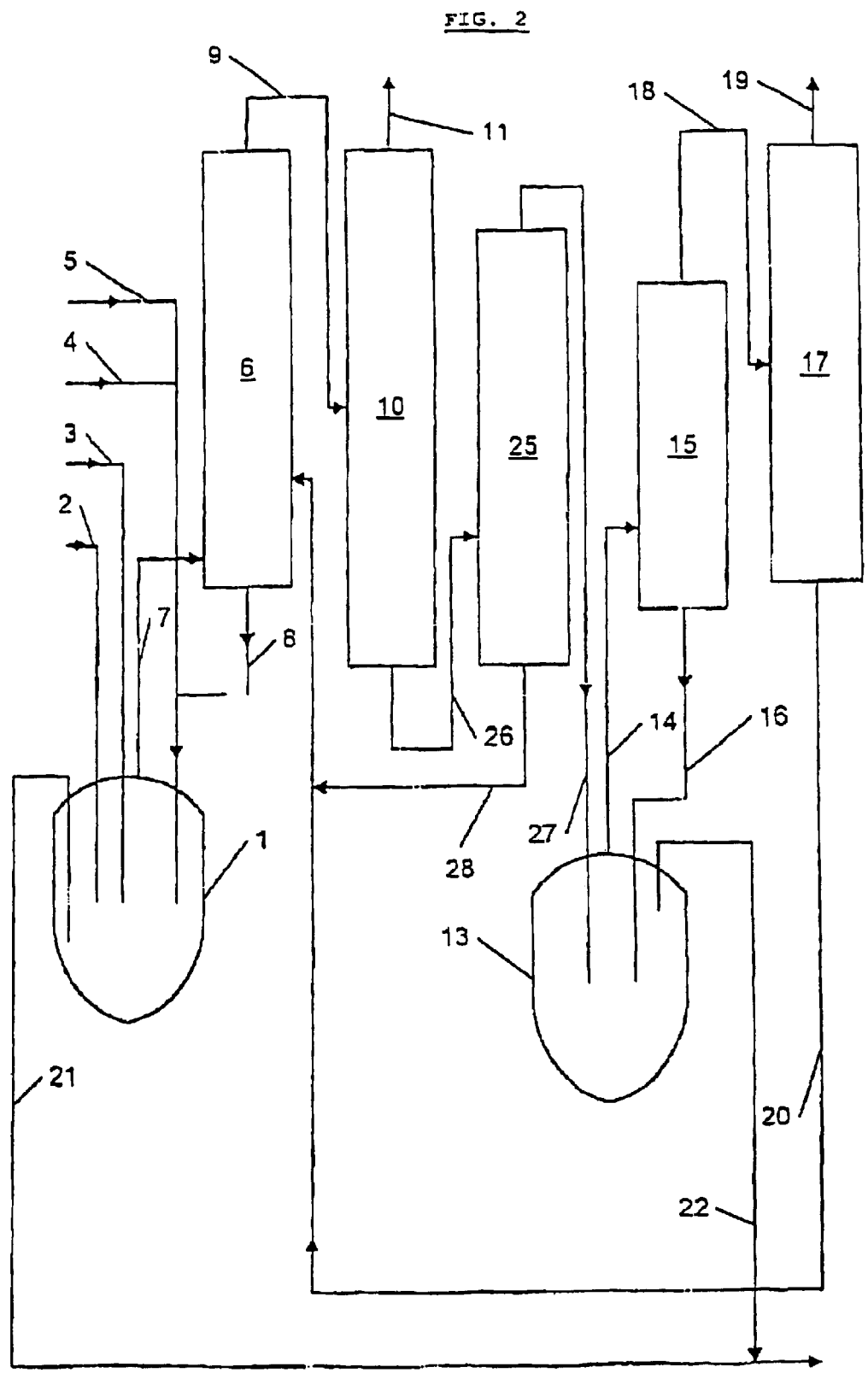

Another embodiment variant, represented in FIG. 2, has been provided.

The parts of this plant which are identical to those of the plant according to Example 1 bear the same reference numbers and these parts will not be described again.

Unlike the plant according to Examples 1 and 2, the product withdrawn from the bottom of the distillation column 10 is conveyed into an intermediate part of an additional distillation column 25 via the pipe 26. It is the head fraction of this column 25 which is conveyed into the post-reactor 13 via the pipe 27. The tail fraction is recycled into the reflux column 6 via the return pipe 28.

This embodiment thus allows yet a further improvement in the reduction of the synthetic intermediates in the product conveyed into the post-reactor 13.

EXAMPLE 4

In a plant corresponding to that described in Example 1, HFC-152a was purified of any vinyl chloride, in the post-reactor 13, by treatment with HF.

The initial composition of the reaction medium (excluding catalyst) in the post-reactor 13, into which the crude HFC-152a is introduced, the operating conditions of the post-reactor and the vinyl chloride contents before and after the post-reactor are given in Table 1 below.

TABLE I

| Composition of the initial reaction medium (excluding catalyst) | Operating conditions of the post-reactor | | | | [VC] inlet ppm | [VC] outlet ppm |
|---|---|---|---|---|---|---|
| | T. (° C.) | P (bar) | [SnCl$_4$] (% by wt.) | Q (g/h.l) | | |
| HF/HFC-152a 50/50% vol. | 65–70 | 12 | 10 | 100 | 60 | <1 |
| HF/PER 33/66% vol. | 88–93 | 10 | 5 | 100–150 | 1700 | <1 |
| | | | | | 10 | <1 |
| HF pure | 93–95 | 10 | 3 | 130–235 | 3000 | <1 |
| | | | | | 1000 | <1 |
| | | | | 200–235 | 8000 | <1 |
| | | | | | 5000 | <1 |

Notes:
Q = feed flow rate of crude HFC-152a per litre of reaction medium
[VC] inlet = weight content of VC in the crude HFC-152a fed into the post-reactor 13
[VC] outlet = weight content of VC in the treated and distilled HFC-152a (pipe 19)
PER = perchloroethylene
[SnCl$_4$] = weight content of SnCl$_4$ relative to the initial reaction medium.

EXAMPLE 5

In this example, the efficacy of a post-reactor 13 in a plant according to Example 1 and of a post-reactor 13 operating under the same conditions, in a plant according to Example 2, were examined. The feed flow rate of crude HFC-152a into the post-reactor was 0.6 kg/h.l.

The average concentrations of VC, HCFC-151a and of HCC-150a, measured at different places in the plant, are reported in Table 2, in mg or g per kilo of HFC-152a.

TABLE 2

|  | VC (mg/kg) | HCFC-151a (g/kg) | HCC-150a (g/kg) |
|---|---|---|---|
| Plant of Example 1 | | | |
| Pipe 9 | 150 | 18 | 4 |
| Pipe 19 | 1.2 | — | — |
| Plant of Example 2 | | | |
| Pipe 9 | 140 | 15 | 4 |
| Pipe 23 | 100 | 4.5 | 0.6 |
| Pipe 19 | 0.6 | — | — |

It emerges clearly from this test that a lowering of the content of 1,1-difluoroethane synthetic intermediates (by more than a half in the present case) in the product subjected to the further treatment in the post-reactor 13 has the effect of drastically reducing the vinyl chloride content in the purified 1,1-difluoroethane.

EXAMPLE 6

In this example, a plant according to Example 2 was run with various flow rates of crude HFC-152a, of from 0.6 to 0.9 kg per hour and per liter of liquid medium in the post-reactor 13.

The results obtained are given in Table 3 below.

TABLE 3

| Flow rate | | Concentration (per kg of HFC-152a) | | |
|---|---|---|---|---|
| of HFC-152a (kg/h.l) | Sampling point | VC (mg/kg) | HCFC-151a (g/kg) | HCC-150a (g/kg) |
| 0.6 | Pipe 9 | 30 | 4.4 | 0.75 |
|  | Pipe 23 | 23 | 2.4 | 0.3 |
|  | Pipe 19 | 0.6 | — | — |
| 0.7 | Pipe 9 | 45 | 7.3 | 1.5 |
|  | Pipe 23 | 42 | 4 | 0.6 |
|  | Pipe 19 | 0.6 | — | — |
| 0.8 | Pipe 9 | 43 | 8 | 1.8 |
|  | Pipe 23 | 41 | 3.9 | 0.6 |
|  | Pipe 19 | 0.7 | — | — |
| 0.9 | Pipe 9 | 52 | 11.7 | 2.9 |
|  | Pipe 23 | 53 | 6.8 | 1.1 |
|  | Pipe 19 | 0.9 | — | — |

It emerges from this table that the purification process remains effective even for high production flow rates.

It should be understood that the present invention is not limited to the embodiments described above and that many modifications can be made thereto without departing from the scope of the attached claims.

What is claimed is:

1. A process for purifying 1,1-difluoroethane of any vinyl chloride, comprising treatment, with hydrogen fluoride, of a crude 1,1-difluoroethane containing less than 1 mol of hydrogen chloride per mole of 1,1-difluoroethane.

2. The process of claim 1, in which the crude 1,1-difluoroethane has, per kg of 1,1-difluoroethane, a 1-chloro-1-fluoroethane content of less than 50 g and a 1,1-dichloroethane content of less than 20 g.

3. The process of claim 1, in which the crude 1,1-difluoroethane is subjected to the said treatment continuously, at a flow rate of from 0.01 to 5 kg per hour and per liter of reaction medium.

4. A process for producing 1,1-difluoroethane, comprising a) a reaction between hydrogen fluoride and a chloro precursor of 1,1-difluoroethane, optionally in the presence of a hydrofluorination catalyst, this reaction giving rise to a crude reaction product which contains vinyl chloride;

b) a separation of hydrogen chloride from the crude reaction product which contains vinyl chloride; and c) a further treatment of the crude reaction product which contains vinyl chloride, which is substantially depleted of HCl, with hydrogen fluoride, this further treatment giving rise to a formation of purified 1,1-difluoroethane.

5. The process of claim 4, wherein the HCl separation is carried out in a distillation column with removal of HCl from the top of the column and withdrawal of the crude reaction product, substantially depleted of HCl, intended for the further treatment, from the bottom of the column.

6. The process of claim 1, in which the treatment is carried out in the liquid phase in a reaction medium containing at least 200 g of HF per kg.

7. The process of claim 1, in which the treatment is carried out in the liquid phase in a reaction medium containing at least 500 g of HF per kg.

8. The process of claim 1, in which the treatment is carried out in the presence of a hydrofluorination catalyst chosen from the group comprising derivatives from groups IIIa, IVa, IVb, Va, Vb or VIb of the Periodic Table of the Elements, and mixtures thereof.

9. The process of claim 8, wherein said catalyst is tin, molybdenum, titanium, vanadium, antimony or tungsten derivative.

10. The process of claim 4, wherein the HCl separation is carried out in a distillation column with removal of HCl from the top of the column, lateral extraction of the crude reaction product substantially depleted of HCl, intended for the further treatment, and withdrawal of a tail fraction containing products heavier than 1,1-difluoroethane.

11. The process of claim 10, further comprising said tail fraction being returned into step a).

12. The process of claim 5, comprising an additional distillation of the said crude reaction product, substantially depleted of HCl, obtained from the said HCl distillation column, with withdrawal, from the top of the column, of the product intended for the further treatment, and withdrawal, from the bottom of the column, of a tail fraction containing products heavier than 1,1-difluoroethane.

13. The process of claim 12, further comprising said tail fraction being returned into step a).

14. The process of claim 4, wherein the crude reaction product contains less than 1 mol of hydrogen chloride per mole of 1,1-difluoroethane.

15. The process of claim 1, wherein the process is carried out in the liquid phase.

16. The process of claim 4, wherein the further treatment is carried out in the liquid phase.

17. The process of claim 1, wherein the crude product is obtained from a synthesis reactor by withdrawing the HCl from the top of a distillation column and the crude product from the bottom.

18. The process of claim 4, wherein the crude product is obtained from a synthesis reactor by withdrawing the HCl from the top of a distillation column and the crude product from the bottom.

19. The process of claim 1, wherein the crude 1,1-difluoroethane contains less than 0.5 mol of hydrogen chloride per mole of 1,1-difluoroethane.

20. The process of claim 4, wherein the crude 1,1-difluoroethane contains less than 0.5 mol of hydrogen chloride per mole of 1,1-difluoroethane.

21. The process of claim 1, wherein the crude 1,1-difluoroethane contains less than 0.1 mol of hydrogen chloride per mole of 1,1-difluoroethane.

22. The process of claim 4, wherein the crude 1,1-difluoroethane contains less than 0.1 mol of hydrogen chloride per mole of 1,1-difluoroethane.

23. The process of claim 1, wherein the crude 1,1-difluoroethane contains less than 0.03 mol of hydrogen chloride per mole of 1,1-difluoroethane.

24. The process of claim 4, wherein the crude 1,1-difluoroethane contains less than 0.03 mol of hydrogen chloride per mole of 1,1-difluoroethane.

* * * * *